United States Patent
Lin

(10) Patent No.: US 7,169,037 B2
(45) Date of Patent: Jan. 30, 2007

(54) AIR CURTAIN APPARATUS FOR OPHTHALMOLOGICAL INSPECTION INSTRUMENT

(76) Inventor: Chin-Liang Lin, 2F No. 45 Lane 24 Sec. 3 Ding Chou Rd., Taipei (TW)

( * ) Notice: Subject to any disclaimer, the term of this patent is extended or adjusted under 35 U.S.C. 154(b) by 274 days.

(21) Appl. No.: 10/458,190

(22) Filed: Jun. 11, 2003

(65) Prior Publication Data

US 2003/0232592 A1    Dec. 18, 2003

(51) Int. Cl.
*F24F 9/00* (2006.01)
(52) U.S. Cl. ...................................... 454/191; 351/245
(58) Field of Classification Search ................ 454/188, 454/191, 66; 351/158, 245
See application file for complete search history.

(56) References Cited

U.S. PATENT DOCUMENTS

| | | | | |
|---|---|---|---|---|
| 3,511,162 A | * | 5/1970 | Truhan | ........................ 454/187 |
| 3,537,447 A | * | 11/1970 | Gauthier et al. | ............ 128/847 |
| 3,935,803 A | | 2/1976 | Bush | |
| 3,998,142 A | | 12/1976 | Foreman et al. | |
| 4,009,647 A | | 3/1977 | Howorth | |
| 4,129,122 A | | 12/1978 | Dout et al. | |

FOREIGN PATENT DOCUMENTS

JP        10028696 A   *  2/1998

* cited by examiner

*Primary Examiner*—Gregory Wilson
(74) *Attorney, Agent, or Firm*—Stevens, Davis, Miller & Mosher, LLP

(57) ABSTRACT

An air curtain apparatus for ophthalmological inspection instrument comprising an air blower installed on the upper side of the support column of the inspection instrument which generates a downward air flow stream in vertical direction, an air suction device installed on the lower side of the support column for sucking the air flow from the air blower which enables an effect of push and pull on the air flow to effectively remove the air exhaled from the ophthalmological patient and diffused around the inspection instrument when the patient sits in front of the eyes-doctor inspection; and the air flow passing through the air suction device is then guided to the Medical lever Air-suction and Cleaning Equipment for filtration and other effective treatment and then discharged to the atmosphere to prevent from inter-infection of germs and odor through breath of air between the eyes-doctor or nursing worker and the patient due to eyes inspection at close distance.

8 Claims, 3 Drawing Sheets

AIR CURTAIN APPARATUS FOR OPHTHALMOLOGICAL INSPECTION INSTRUMENT

BACKGROUND OF THE PRESENT INVENTION

1. Field of the Present Invention

The invention relates to an air curtain apparatus for ophthalmological inspection instrument, and more particularly to an apparatus installed on the support columns of the ophthalmological inspection instrument which generates an air flow stream acted by push and pull force to prevent the inter-infection of germs and odor through breath of air between eyes-doctor or nursing worker and the patient due to eyes inspection sitting at close distance.

2. Description of Prior Art

Most inspection instruments used in ophthalmological department have a common feature of very close distance between eyes-doctor or nursing worker and the patients. Normally when eyes-doctor or nursing worker inspects the eyes of patient using inspection instrument, the eyes-doctor or nursing worker always sits at close distance to the patient across the inspection instrument. There is no any isolating equipment or protecting measure between them, or even if there is such kind of equipment or measure, the effect of protection is always slim, and restricted to some limited extend. Owing this reason it is impossible to prevent the air exhaled by the patient from diffusing to the space surrounding the eyes-doctor, and the unexpected inter-infection is therefore unavoidable if the patient carries hazardous germs or odor. Similarly, the patient under ophthalmological inspection will suffer the same inter-infection when the doctor or nursing worker caries hazardous germs or odor.

Therefore, if the air surrounding the inspection instrument can be treated to remove the potentially hazardous germs or odor contained in the air using filtration and cleaning equipment, the inter-infection between eyes-doctor, nursing worker and patient can be avoided.

SUMMARY OF THE PRESENT INVENTION

The major purpose of the invention is to provided an air-curtain apparatus for ophthalmological inspection instrument to prevent the eyes-doctor or nursing worker and patient from getting infected by the germs and odor carried by each of them. The key technique of the invention is the application of the principles of generating a push and pull effect on air flow to move away the air exhaled by eyes-doctor or nursing worker and patient under ophthalmological inspection from the space surrounding the inspection instrument to prevent the eyes-doctor or nursing worker and patient from being exposed to the detrimental working environment.

The minor purpose of the invention is to provide an air-curtain apparatus for ophthalmological inspection instrument by applying an air blower to generate a downward air flow stream in vertical direction under the pushing force exerted by the air blower and an air suction device for pulling down the air flow stream to form the effect of push and pull which can move away the air exhaled by the patient under ophthalmological inspection and the eyes-doctor or nursing worker from the environment surrounding the inspection instrument to ensure the health of them.

Another purpose of the invention is the application of a medical level air-suction and cleaning equipment which is connected to the air suction device to generate an effect of suction exerted by the air suction device on the downward air flow stream and to serve as a guide for guiding the air flow to the medical level air-suction and cleaning equipment to remove the hazardous germs or odor contained in the air by means of filtration and other effective process to eliminate the secondary pollution.

BRIEF DESCRIPTION OF THE DRAWING FIGURES

DETAILED DESCRIPTION OF THE PREFERRED EMBODIMENTS

The air-curtain apparatus for ophthalmological inspection instrument can be applied on the inspection instruments including Slit-lamp Microscope, Auto-Refractometer, Tonometer, Fundus Camera, IOL, Intra Ocular Lenses Biometer, Specular Microscope, Retian Laser Scan Angiograph, Orbscan and Wave Scan, Wave Front System etc.

As for the sake of convenience the application of the present invention on slit-lamp microscope is selected as one of the preferred embodiments of the invention, and is illustrated in the following description for making better understanding of the invention. However, the scope of patent claimed herein shall cover the application of the invention on inspection instruments in ophthalmological department as mentioned above.

Figure 1:
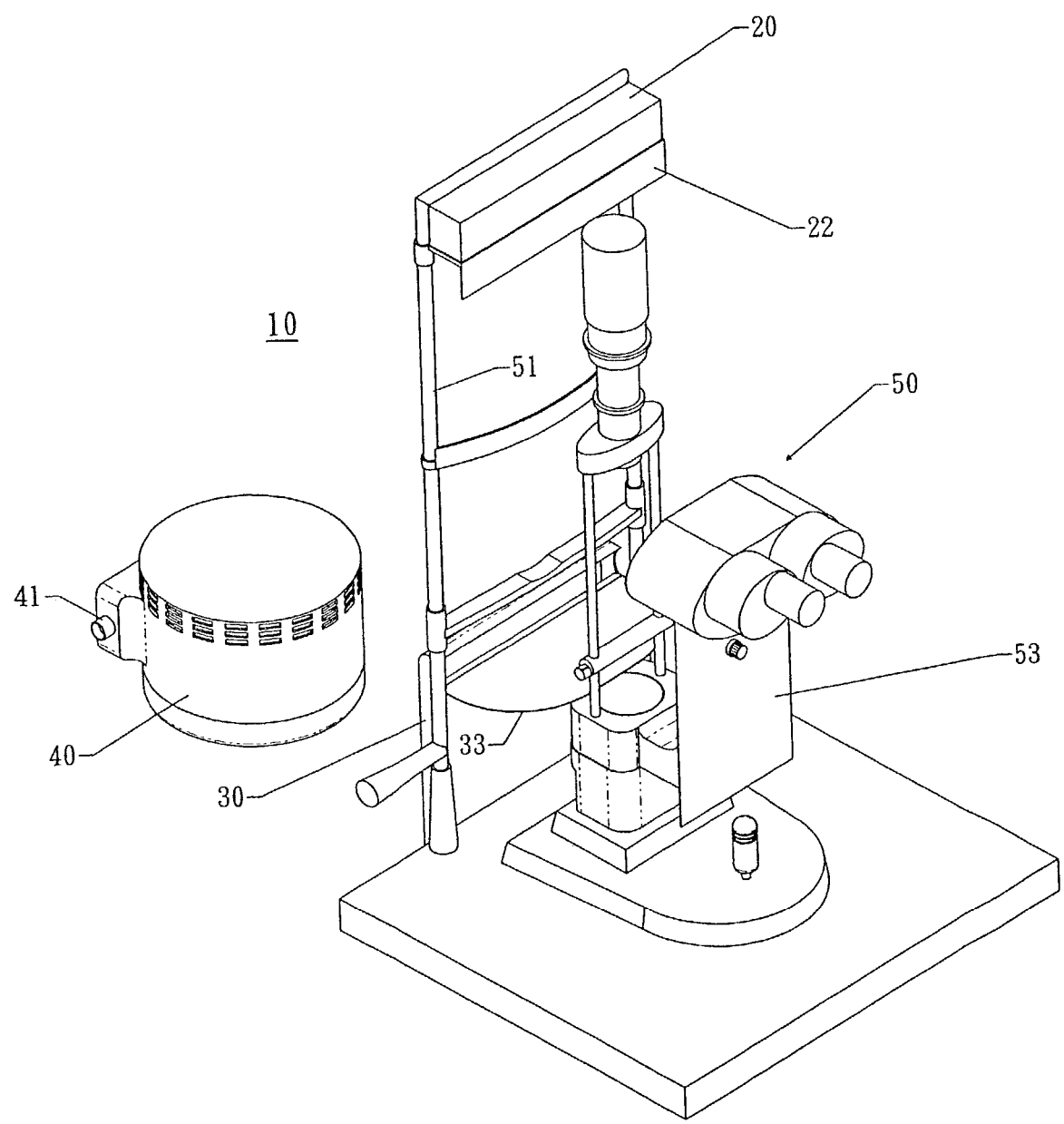
FIG. 1 is the assembly drawing of the air-curtain apparatus for ophthalmological inspection instrument of the invention applied on the slit-lamp microscope.
Figure 4:
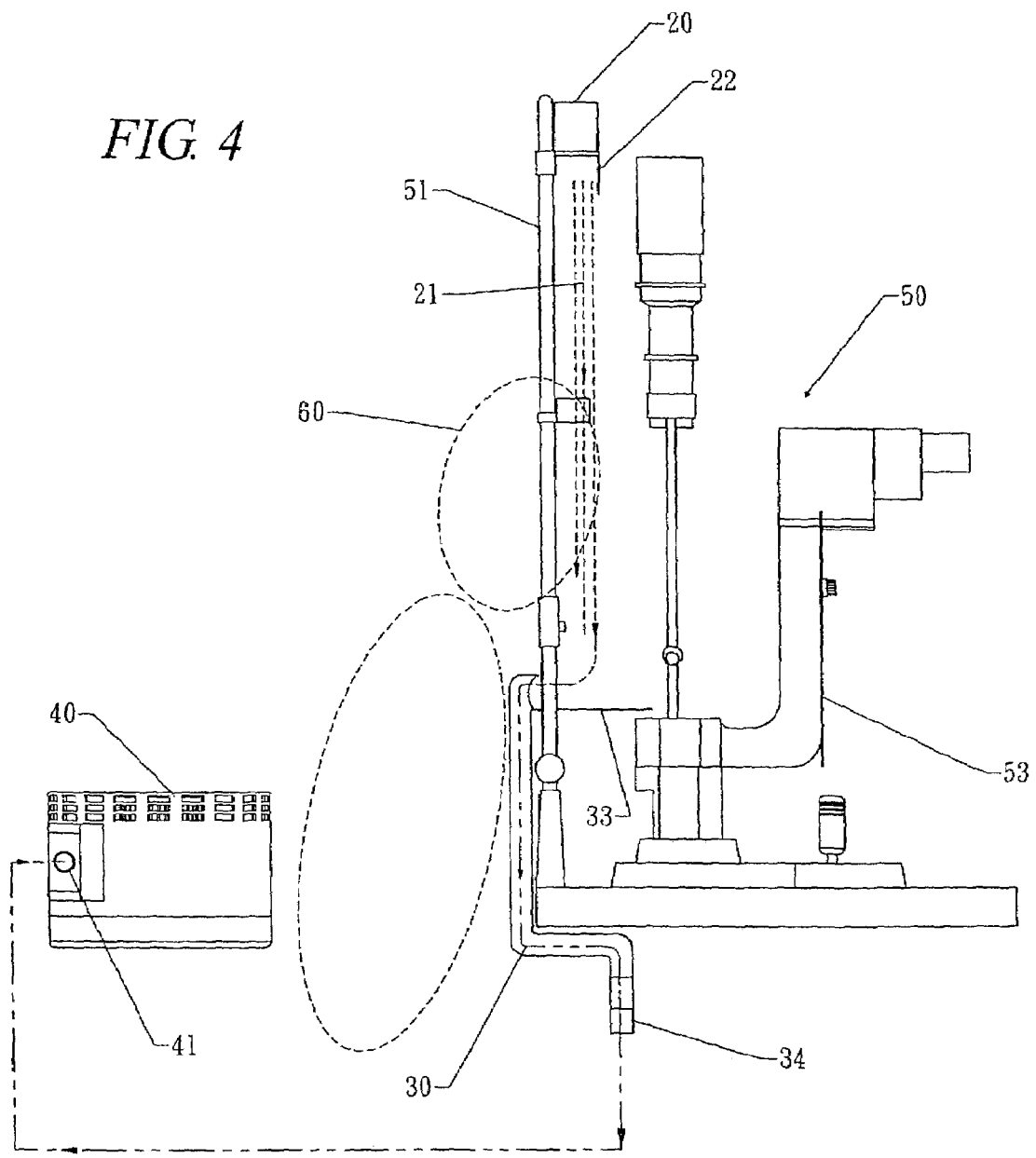
FIG. 4 is the aspect view of the air-curtain apparatus for ophthalmological inspection instrument in operation.

Please refer to FIG. 1 and FIG. 4, the air-curtain apparatus (10) of the invention applied on slit-lamp microscope comprises an air blower (20), an air suction device (30) connected to an air duct assembly (not shown in the drawing) and an air-suction and cleaning equipment (40) in which the air blower (20) and air-suction and cleaning equipment (40) are installed and fastened respectively on the upper and lower side of the support column of the slit-lamp microscope (50) (or the afore-said inspection instruments in ophthalmological department). When the patient (60) sits in front of the slit-lamp microscope (50) for eyes examination, an air flow stream (21) is continuously delivered downwardly passing through the space in front of the head of the patient that generates an effect of pushing the air stream in downward direction which can immediately push the air exhaled by the patient (60) for ophthalmological inspection, and carry the air flow (21) to the inlet of the air suction device (30), and the pulling effect generated by suction device (30) on the air flow can pull the air flow (21) away from the space surrounding the slit-lamp microscope (50), and send the air into the air-suction and cleaning equipment (40) to remove the hazardous germs or odor through filtration process and other effective treatment, and then the clean air is exhausted to the atmosphere. The said air blower (20) is a rectangular shaped blower installed on the upper side of the support column (51) of the slit-lamp microscope (50), a guide plate (22) is located at the front edge of the outlet of the air blower (20), and is in a position parallel to the air flow which can guide the air flow (21) to move steadily in downward direction when the motor of the air blower (20) is turned on. Therefore, when the patient (60) is sitting in front of the slit-lamp microscope (50), the air flow (21) from air blower (20) generates an effect of push and scour which bring away the air in the surround of the head of the patient (60), and move it all the way down including the air exhaled by the patient (60) to form an air stream (21) without any of them flowing and diffusing to the space surrounding the eyes-doctor or nursing worker.

Moreover, in order to achieve the effect of push and pull, a suction device (30) is installed beneath the air blower (20), and mounted on the appropriate position on the lower side of the support column (51) in the front side of the slit-lamp microscope (50). The operation of the medical level air-suction and cleaning equipment (40) causes the suction device (30) to exert a negative pressure on the air flow (21) which can completely absorb and remove the air exhaled by the patient (60) from the space surrounding the slit-lamp microscope (50).

Figure 2:
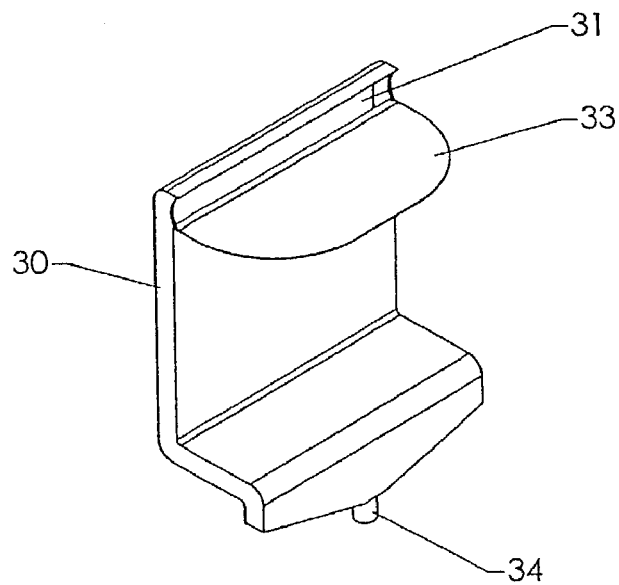
FIG. 2 shows the three-dimensional structure of the air suction device of the invention.
Figure 3:
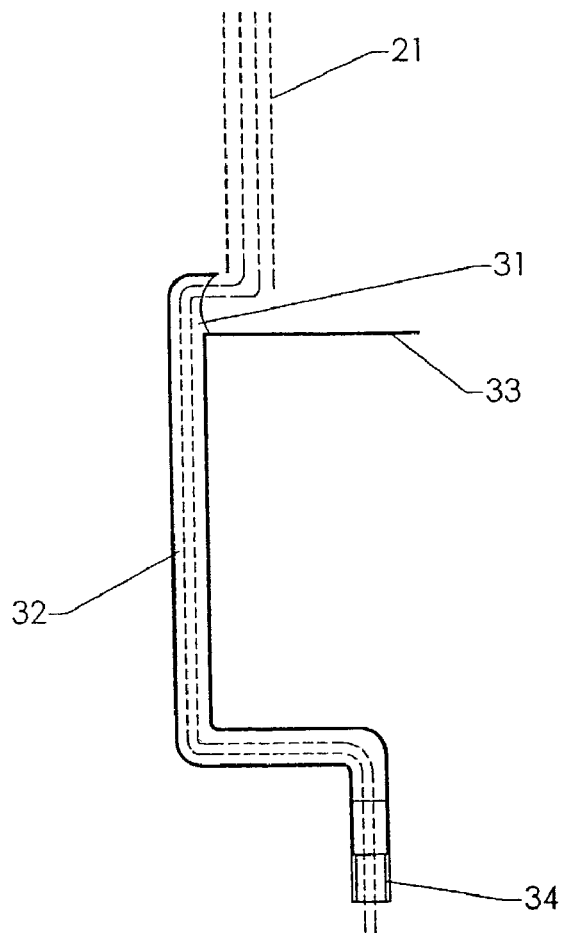
FIG. 3 is the scale-enlarged cross sectional view of the component of air suction device shown in FIG. 2.

As shown in FIG. 2 and FIG. 3 are the construction drawing and cross sectional view of the said air suction device (30) which is provided with a hallow inner side forming air flow duct (32) constructed by thin plate wall. A slot-shaped air inlet (31) is located at and connected to the upper end of the air flow duct (32) with a buffer plate (33) located at and extended from the edge of the lower lip of the air inlet (31). The said buffer plate (33) is made of soft plastic material or rubber or the similar material for buffing air-flow (21) and conducting the air flow toward the slot-shaped air inlet (31) where a negative pressure is formed inside. A tube connector (34) is mounted to and extended from the end of the outlet located on the underside of the suction device (30) serving as the outlet of the air flow duct and the connection for connecting the air tube and air-suction and cleaning equipment (40).

The air-suction and cleaning equipment (40) used in the invention may be the medical level air-suction and cleaning equipment which has a inlet connector (41) and build-in disinfection and filtration equipment such as air filter, ultra-violet ray and other disinfection means, and the air outlet hole (42) on the side wall. When the air-suction and cleaning equipment is in operation, air can only enters the equipment through the air inlet connector (41), and the clean air is exhausted to the atmosphere after completing the disinfection and filtration process.

Now refer to FIG. 4, when the air curtain apparatus (10) installed on the slit-lamp microscope or other related inspection instrument in ophthalmological department is turned on, the air flow (21) from the air blower (20) moving downwardly in vertical direction is buffed and guided by the buffer plate (33) of the suction device (31), and pulled by the slot-shaped inlet (31) that can effectively remove the hazardous germs and odor contained in the air exhaled by the patient (60) to the surround of the slit-lamp microscope by the effect of push and pull exerted on the air flow, and then the air is sent to the medical level air-suction and cleaning equipment (40) for disinfection and filtration treatment before exhausting to the atmosphere. By applying the invention, the inter-infection of germs or odor between eyes-doctor or nursing worker and the patient (60) can be avoided when carrying out ophthalmological inspection.

Further, shown in FIG. 1 and FIG. 4, are another preferred embodiment of the invention in which an isolating plate (53) is installed on the swivel rod (52) of the lens frame with upper edge of the isolating plate (53) positioned closed to the lower edge of the eyes-pieces of the slit-lamp microscope to serve as the secondary protection of eyes-doctor to further minimize the risk of having eyes-doctor be infected by germs.

In addition, one more preferred embodiment is to install the air blower (20) on the lower side of the support column (51) of the slit-lamp microscope, and the air flow is in upward direction, but the air suction device (50) is installed in upside-down position on the upper side of the support column (51) of the slit-lamp microscope (50) and is connected to the medical level air-suction and cleaning equipment (40) to enable an effect of pull and push on the air flow by way of blowing from lower side and suction from upper side.

What is claimed is:

1. An air curtain apparatus for an ophthalmological inspection instrument, the air curtain apparatus comprising:
   an air blower,
   an air suction device connected to medical level air-suction and cleaning equipment through an air flow duct for pushing, pulling and filtrating the air existing in the front side of the ophthalmological inspection instrument, wherein
   the air blower is installed on the upper side of a pair of support columns of the ophthalmological inspection instrument for generating an air flow stream downwardly in a vertical direction; and
   the air suction device is installed on the lower side of the support columns of the ophthalmological inspection instrument and includes: (1) a hollow inner side constructed of a thin sheet material to form the air flow duct, (2) a slot-shaped opening as an air inlet connected to the air flow duct, (3) a buffer plate extending from the lower edge of the slot-shaped opening, and (4) a tube connector as an air outlet through which the air suction device is connected to the air-suction and cleaning equipment.

2. The air curtain apparatus, for the ophthalmological inspection instrument as described in claim 1, wherein the air blower further m comprises an air flow guide plate to regulate the flowing direction of air flow out from the air blower.

3. The air curtain apparatus for the ophthalmological inspection instrument as described in claim 1, wherein the slot-shaped opening is opened on the side end of the air suction device.

4. The air curtain apparatus for the ophthalmological inspection instrument as described in claim 1, further comprising an isolating plate installed on a swivel rod of a lens-frame of the ophthalmological inspection instrument.

5. An air curtain apparatus for an ophthalmological inspection instrument, the air curtain apparatus comprising:
   an air blower,
   an air suction device connected to medical level air-suction and cleaning equipment through an air flow duct for pushing, pulling and filtrating the air existing in the front side of the ophthalmological inspection instrument; wherein
   the air blower is installed on the lower side of a pair of support columns of the ophthalmological inspection instrument for generating an upward air flow stream in the vertical direction, and
   the air suction device is installed in an upside-down position on the upper side of the support columns of the ophthalmological inspection instrument and includes: (1) a hollow inner side constructed by of a thin sheet material to form the air flow duct, (2) a slot-shaped opening as an air inlet connected to the air flow duct, (3) a buffer plate extending from the lower edge of the slot-shaped opening, and (4) a tube connector as an air outlet through which the air suction device is connected to the air-suction and cleaning equipment.

6. The air curtain apparatus for the ophthalmological inspection instrument as described in claim 5, wherein the air blower further has an air flow guide plate to regulate the flowing direction of air flow out from the air blower.

7. The air curtain apparatus for the ophthalmological inspection instrument as described in claim 5, wherein the slot-shaped opening is opened on the side end of the air suction device.

8. The air curtain apparatus for the ophthalmological inspection instrument as described in claim 5, further comprising an isolating plate installed on a swivel rod of a lens-frame of the ophthalmological inspection instrument.

* * * * *